United States Patent
Goruganthu et al.

(10) Patent No.: US 6,350,624 B1
(45) Date of Patent: Feb. 26, 2002

(54) SUBSTRATE REMOVAL AS A FUNCTIONAL OF SONIC ANALYSIS

(75) Inventors: Rama R. Goruganthu; Jeffrey D. Birdsley; Michael R. Bruce; Brennan V. Davis; Rosalinda M. Ring, all of Austin, TX (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/409,304

(22) Filed: Sep. 29, 1999

(51) Int. Cl.$^7$ ............................................. H01L 21/302
(52) U.S. Cl. ............................................................ 438/5
(58) Field of Search ............................. 438/5, FOR 141

(56) References Cited

U.S. PATENT DOCUMENTS

| | | | |
|---|---|---|---|
| 5,240,552 A | * | 8/1993 | Yu et al. |
| 5,279,316 A | * | 1/1994 | Miranda |
| 5,439,551 A | * | 8/1995 | Meikle et al. |
| 5,500,073 A | * | 3/1996 | Barbee et al. |
| 5,503,707 A | * | 4/1996 | Maung et al. |
| 5,579,792 A | * | 12/1996 | Stanasolovich et al. |
| 6,148,833 A | * | 11/2000 | Tang et al. |
| 6,194,230 B1 | * | 2/2001 | Li et al. |
| 6,228,769 B1 | * | 5/2001 | Li et al. |

* cited by examiner

Primary Examiner—George Fourson
Assistant Examiner—Joannie Adelle Garcia

(57) ABSTRACT

Substrate removal for post-manufacturing analysis of a semiconductor device is enhanced via a method and system that use sonic energy in the control of the removal process. According to an example embodiment of the present invention, sonic energy is reflected off of a region of a semiconductor chip having a portion of substrate removed from the back side of the chip. The reflections are detected and used to determine the thickness of substrate in the back side. In this manner, the substrate removal process can be efficiently and accurately controlled.

9 Claims, 4 Drawing Sheets

SUBSTRATE REMOVAL AS A FUNCTIONAL OF SONIC ANALYSIS

FIELD OF THE INVENTION

The present invention relates generally to semiconductor chips and their fabrication and, more particularly, to post-manufacturing testing of semiconductor chips involving substrate removal.

BACKGROUND OF THE INVENTION

The semiconductor industry has recently experienced technological advances that have permitted dramatic increases in circuit density and complexity, and equally dramatic decreases in power consumption and package sizes. Present semiconductor technology now permits single-chip microprocessors with many millions of transistors, operating at speeds of hundreds of millions of instructions per second to be packaged in relatively small, air-cooled semiconductor device packages. A by-product of such highdensity and high functionality in semiconductor devices has been the demand for increased numbers of external electrical connections to be present on the exterior of the die and on the exterior of the semiconductor packages which receive the die, for connecting the packaged device to external systems, such as a printed circuit board.

To increase the number of pad sites available for a die, to reduce the electrical path to the pad sites, and to address other problems, various chip packaging techniques have been developed. One of these techniques is referred to as controlled collapse chip connection or flip-chip packaging. With packaging technology, bonding pads of the die include metal (solder) bumps. Electrical connection to the package is made when the die is flipped over and soldered to the package. Each bump connects to a corresponding package inner lead. The resulting packages are low profile and have low electrical resistance and a short electrical path. The output terminals of the package, which are sometimes ball-shaped conductive bump contacts, are typically disposed in a rectangular array. These packages are occasionally referred to as Ball Grid Array (BGA) packages. Alternatively, the output terminals of the package may be pins and such packages are commonly known as pin grid array (PGA) packages.

Once the die is attached to such a package the back side portion of the die remains exposed. The transistors and other circuitry are generally formed in a very thin epitaxially-grown silicon layer on a single crystal silicon wafer from which the die is singulated. The side of the die including the epitaxial layer containing the transistors and other circuitry is often referred to as the circuit side or front side of the die. The circuit side of the die is positioned very near the package and opposes the back side of the die. Between the back side and the circuit side of the die is single crystalline silicon.

The positioning of the circuit side near the package provides many of the advantages of the flip chip. However, in some instances orienting the die with the circuit side face down on a substrate is disadvantageous. Due to this orientation of the die, the transistors and circuitry near the circuit side are not directly accessible for testing, modification or other purposes. Therefore, access to the transistors and circuitry near the circuit side is from the back side of the chip.

Techniques have been developed to access the circuit even though the integrated circuit (IC) is buried under the bulk silicon. For example, near-infrared (nIR) microscopy is capable of imaging the circuit because silicon is relatively transparent in these wavelengths of the radiation. To acquire these images, because of the absorption losses of IR radiation in silicon, it is generally required to thin the die to less than 100 microns. For example, on a die that is 725 microns thick, at least 625 microns of silicon is typically removed before IR microscopy can be used. Thinning the die for failure analysis of a flip chip bonded IC is usually accomplished by first thinning the die across the whole die surface, often referred to as global thinning. Mechanical polishing, such as chemical-mechanical polishing (CMP), is one method for global thinning.

Once an area is identified using IR microscopy as an area of interest and it is determined that access is needed to a particular area of the circuit, local thinning techniques are often used to thin an area smaller than the die size. One method of local thinning, referred to as laser microchemical etching, is typically accomplished by focussing a laser beam on the back side of the silicon surface to cause local melting of silicon in the presence of chlorine gas. The molten silicon reacts very rapidly with chlorine and forms silicon tetrachloride gas, which leaves the molten (reaction) zone. This is a silicon removal process used in connection with the 9850 SiliconEtcher™ tool by Revise, Inc. (Burlington, Mass). This laser process is suitable for both local and global thinning by scanning the laser over a part or whole surface of the die.

During failure analysis, or for design debug, it is sometimes desirable to make electrical contact and probe certain circuit nodes on the circuit side or front side of a die, or to reconfigure the conductors in an integrated circuit. This access is generally done by milling through substrate to access the node, or milling to the node and subsequently depositing a metal to electrically access the node. Often, global and local thinning as described above are used to accomplish such milling. Accurate determination of the thickness of the silicon in the backside, however, is not readily achieved, making the milling process difficult to control. When not controlled properly, substrate removal can result in damage to or destruction of circuitry in the device. In particular, it is important to have the ability to determine the endpoint of the removal process with sufficient accuracy to avoid milling off the node to which access is being sought, which could often jeopardize further device analysis. In addition to knowing when to stop the removal process, it is also important to know how far the removal process has proceeded in order to more efficiently and more accurately control the removal process.

SUMMARY OF THE INVENTION

The present invention is directed to a method and system for post-manufacturing analysis of a semiconductor device involving controlling substrate removal from the device using sonic energy. The present invention is exemplified in a number of implementations and applications, some of which are summarized below.

According to an example embodiment, the present invention includes a method for removing substrate from a semiconductor chip for post-manufacturing analysis. Sonic energy is reflected off of a region of the semiconductor chip and detected. A portion of substrate in the back side of the semiconductor chip is removed as a function of the detected sonic energy. In this manner, the substrate removal process can be efficiently and accurately controlled.

According to another example embodiment of the present invention, a system is arranged to remove substrate from a semiconductor chip having a back side opposite circuitry near a circuit side. A substrate removal device including a controller is arranged to remove substrate from the back side of the chip. The chip is immersed in a tank having liquid. A sonic energy generating device is arranged to direct sonic energy at the back side of the chip via the liquid, and a detection device is adapted to detect the sonic energy as it reflects from the chip and through the liquid. A computer arrangement is coupled to the detection device and to the controller and adapted to interpret the detected sonic energy and to send a signal to the controller responsive to the interpreted sonic energy.

The above summary of the present invention is not intended to describe each illustrated embodiment or every implementation of the present invention. The figures and detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
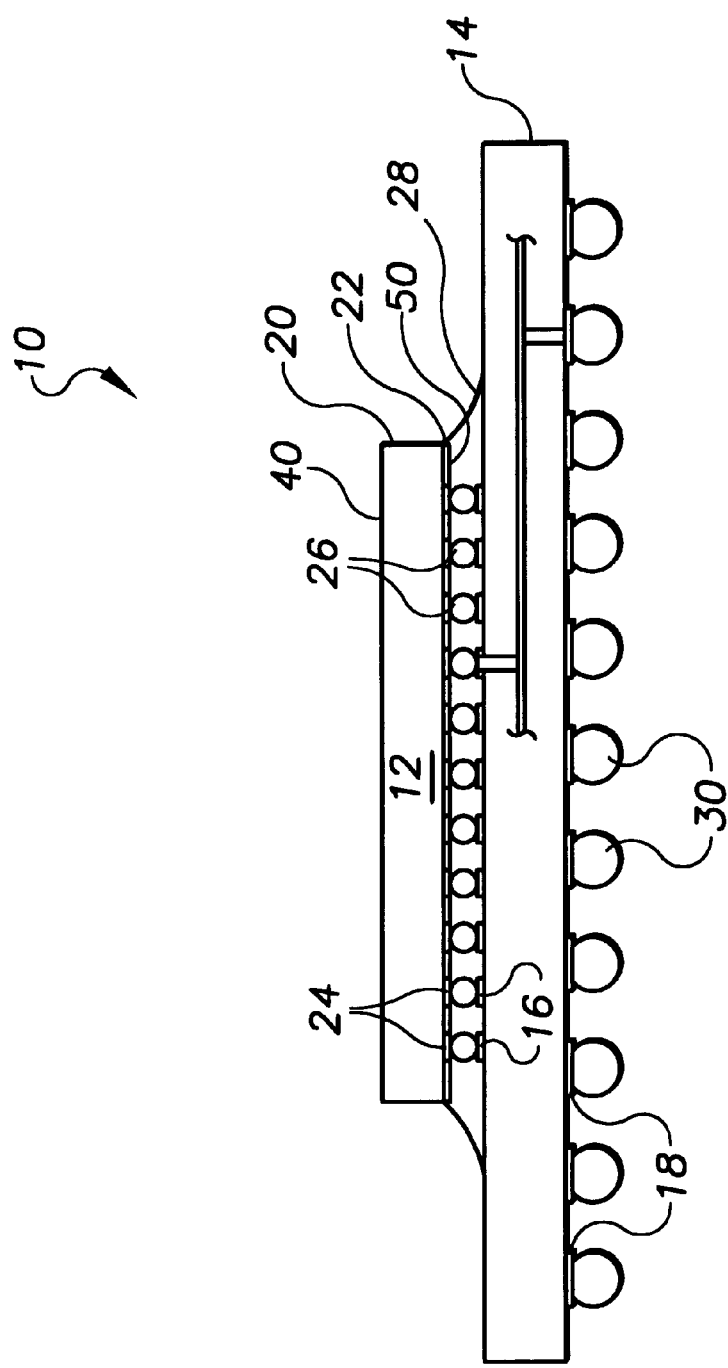
FIG. 1 is a flip-chip type semiconductor device for use in connection with the present invention.

While the invention is amenable to various modifications and alternative forms, specifics thereof have been shown by way of example in the drawings and will be described in detail. It should be understood, however, that the intention is not necessarily to limit the invention to the particular embodiments described. On the contrary, the intention is to cover all modifications, equivalents, and alternatives falling within the spirit and scope of the invention as defined by the appended claims.

DETAILED DESCRIPTION

The present invention is believed to be applicable for a variety of different types of semiconductor devices, and the invention has been found to be particularly suited for flip-chip and other type devices requiring or benefiting from post-manufacturing analysis involving substrate removal. While the present invention is not necessarily limited to such devices, various aspects of the invention may be appreciated through a discussion of various examples using this context.

In connection with an example embodiment of the present invention, it has been discovered that the reflection of sonic energy directed at a semiconductor chip submersed in a liquid is useful for controlling substrate removal from the chip. The reflection varies according to the region of the chip from which the energy is reflected. This variation in reflected energy can be detected and used for determining the progression of the substrate removal process, including determining the endpoint of the process.

According to a more particular example embodiment of the present invention, a portion of substrate is removed from the back side of a semiconductor chip. The chip is placed in a tank having liquid, such as water. A sonic source is arranged over the back side of the chip and used to direct sonic energy at the back side of the chip via the liquid. The energy reflects from the chip and is detected via a detector. Energy reflects differently from distinct regions of the chip, and the difference in reflections is used to determine the depth of the region from which the reflection came from. For instance, sonic energy reflecting directly off of the back side surface of the device reaches the detector before reflections from regions deeper in the chip, such as from circuitry within the device or from an exposed region where substrate has been removed. The difference in the time it takes a reflection to reach the detector is measured and used to determine the depth of the region. One method for determining the depth involves using the speed of the sonic energy wave and multiplying that speed by the time differential between detected reflections from the back side surface and a region in the device to provide an indication of the depth of the region. In this manner, the thickness of substrate between the back side surface and other regions in the device can be determined.

This method for removing substrate for post-manufacturing analysis of a semiconductor chip is applicable to a variety of semiconductor devices. For example, FIG. 1 shows a side view of an assembly 10 of one type of conventional flip chip type die 12 assembled to a package substrate 14. Flip chip die 12 has a circuit side 50 and a back side 40. The circuit side 50 includes a number of circuit devices formed near the circuit side in a portion of the die known as the epitaxial layer 22. The epitaxial layer 22 has a thickness in the range of 1 to 15 microns. The portion of the die shown above the epitaxial layer is known as the bulk layer 20. A plurality of solder bumps 26 are made on the circuit side 50 at pads 24. The solder bumps 26 are the inputs and outputs to the circuitry associated with the die 12.

The flip chip type die 12 is attached to package substrate 14, such as a package for a flip chip via the solder bumps on the die 12. The package substrate 14 includes pads 16 which are arranged to correspond to the pattern of solder bumps on the die 12. The region between integrated circuit 12 and package substrate 14 is filled with an under-fill material 28 to encapsulate the solder bump connections and provide additional mechanical benefits. The pads 16 are coupled via circuitry to pads 18 on the package substrate. Solder bumps 30 are formed on the pads 18. The solder bumps 30 are the inputs and outputs to the circuitry associated with the package substrate 14. In another arrangement (not illustrated), the inputs and outputs to the circuitry associated with the package substrate 14 are implemented as pins rather than solder bumps.

Figure 2:
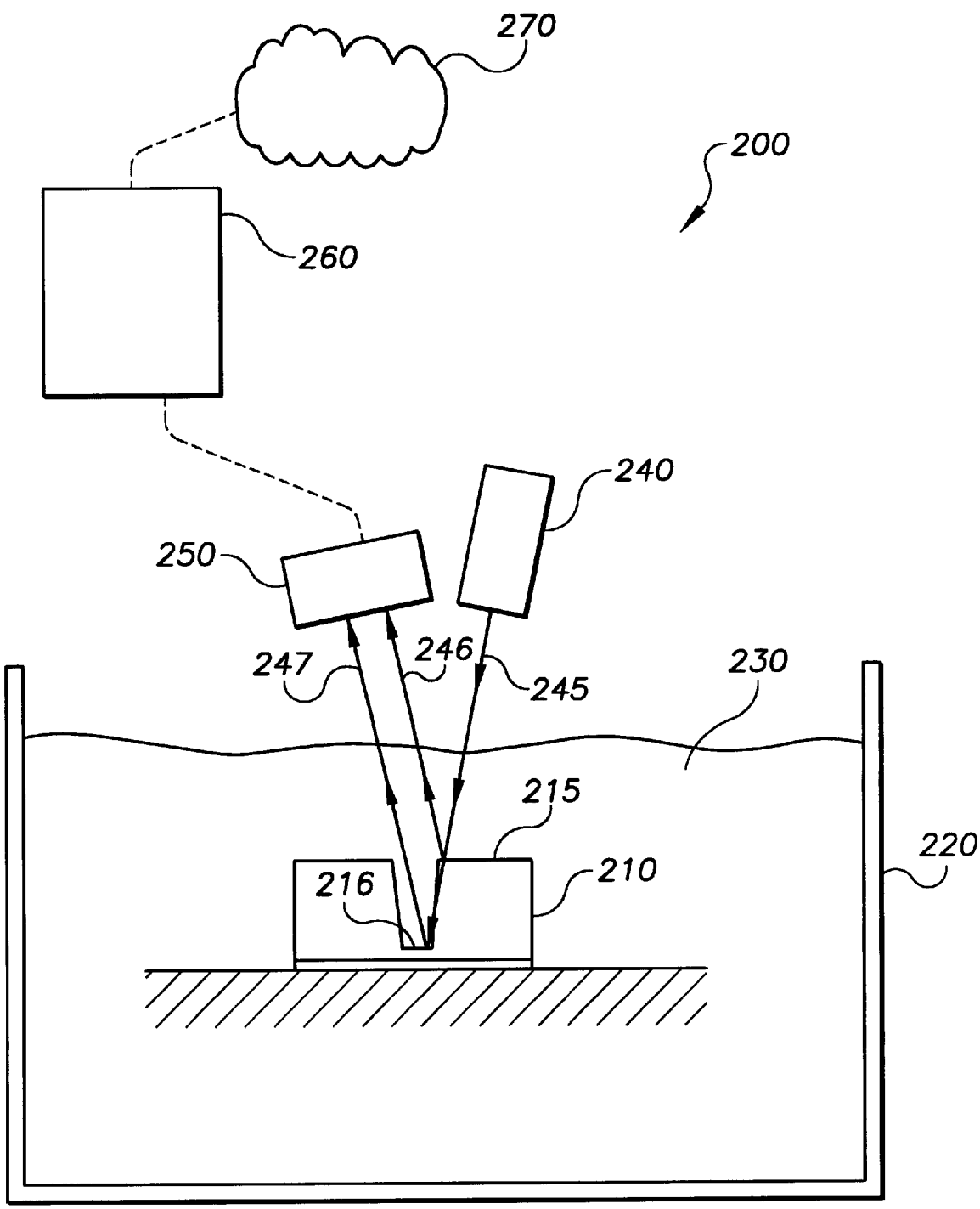
FIG. 2 shows a semiconductor device undergoing analysis, according to an example embodiment of the present invention.

According to another example embodiment of the present invention, FIG. 2 shows a semiconductor device 210 undergoing post-manufacturing analysis. The semiconductor device 210 may, for example, be a flip chip device such as shown in FIG. 1, or another type of integrated circuit device. A portion of the semiconductor device 210 has been removed to form an exposed region 216 below a back side surface 215. The semiconductor device 210 is immersed in a tank 220 of liquid 230. A sonic energy generating device 240 is arranged over the tank 220 and used to direct sonic energy 245 at the semiconductor device 210. A portion of the sonic energy 245 reflects off of the back side surface 215 to a detection device 250 as reflected energy 246. Another portion of the sonic energy 245 reflects off of the exposed region 216 to the detection device 250 as reflected energy 247. The two reflected portions are detected at the detector 250, and the time differential between their arrival at the detector 250 is measured and used to determine the depth of the exposed region 216 relative to the back side surface 215. In an alternative embodiment, the sonic energy generating device 240 and the detector 250 are included in a single arrangement.

Figure 3:
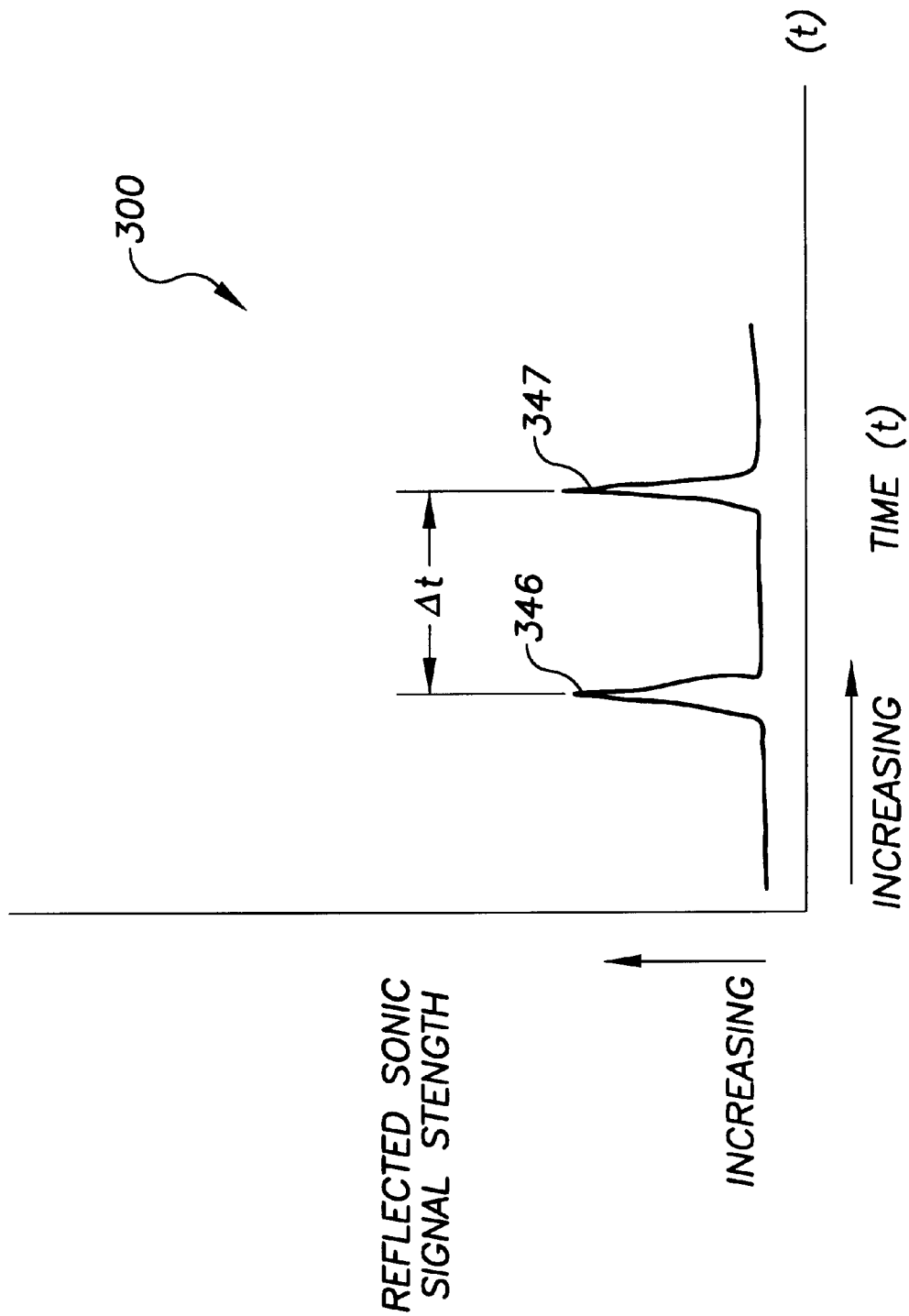
FIG. 3 is an example graph showing reflected sonic strength versus time, according to another example embodiment of the present invention.

FIG. 3 shows a graph 300 depicting an example signal strength versus time (t) measurement that can be made by the detection device 250 shown in FIG. 2. Reflection 246 is represented in the graph as spike 346, and reflection 247 is represented in the graph as spike 347. Spike 347 is received at a time $\Delta t$ after spike 346. Using the time differential between the spikes and the speed of the sonic energy in the liquid 230, the depth of the exposed region 216 can be determined. For example, if the liquid 230 is water at 20° C., the speed of sound through the liquid is 1470 m/sec. By using the equation $d=\Delta t * 1470$ m/sec, measuring $\Delta t$ and solving for d (depth), the result is the depth in meters of the exposed region 216.

According to another example embodiment of the present invention, and referring again to FIG. 2, the detection device 250 is coupled to a computer arrangement 260 which is programmed to interpret the detected energy, such as by using the equation above to determine the depth of the exposed region 216. In another implementation, the computer arrangement 250 is further coupled via circuitry to a substrate removal arrangement 270 having a controller and programmed to control the substrate removal process via the controller in response to the determined depth of the exposed region 216.

Figure 4:
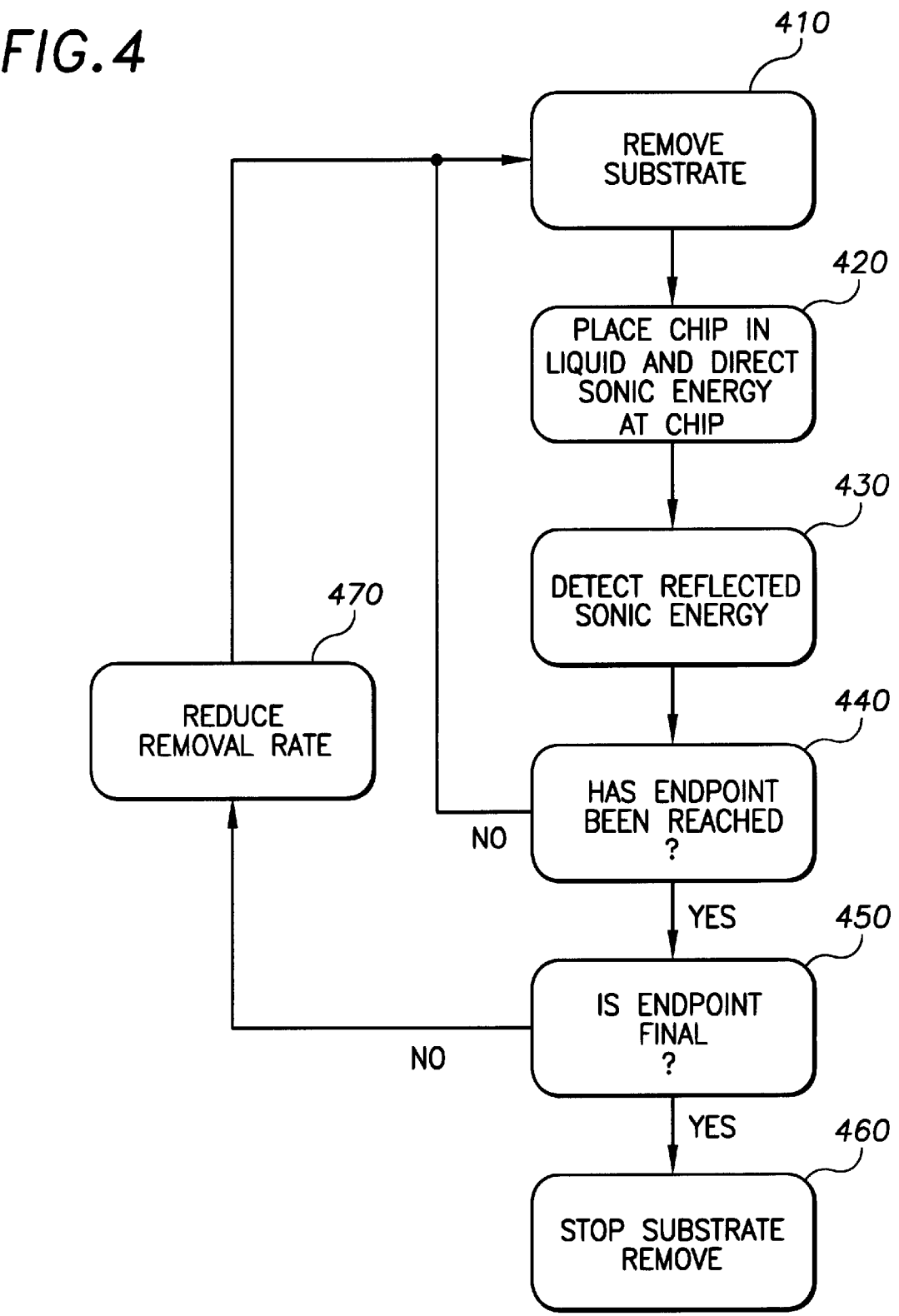
FIG. 4 is a flow chart for a method for post-manufacturing analysis of a semiconductor chip, according to another example embodiment of the present invention.

FIG. 4 is a flow chart for a method of removing substrate from a semiconductor device, according to another example embodiment of the present invention. A portion of substrate is removed from a semiconductor chip and an exposed region is formed at block 410. The substrate removal can be accomplished using a device such as a focused ion beam (FIB) or other ion bombardment device, a laser etching device, or a chemical-mechanical polishing device. The chip is placed in liquid and sonic energy is directed at the chip at block 420 using a sonic energy source such as an UltraSonic Transducer available from Sonix, Inc. At block 430, sonic energy reflected off of the chip is detected and used to determine the thickness of substrate in the chip at the exposed region. The reflected energy can be detected using a device such as an UltraSonic Transducer available from Sonix, Inc.

At block 440, it is determined if an endpoint has been reached. An endpoint may, for instance, be associated with a particular depth of substrate removal. If no endpoint has been reached, the chip is removed from the liquid and the method continues at block 410. If an endpoint has been reached at block 440, it is determined if the endpoint is final. A final endpoint is associated with the end of the substrate removal process. A non-final endpoint may be associated with nearing the final endpoint, such as a point in the substrate removal process where it is desirable to slow the substrate removal rate so as not to exceed the final endpoint and damage the chip. If the endpoint is not final at block 450, the substrate removal rate is reduced at block 470 and the chip is removed from the liquid and the method continues at block 410. If the endpoint at block 450 is final, the substrate removal is stopped at block 460. The rate at which substrate is removed can be determined as a function of the semiconductor device and the removal process, and controlled to proceed as fast as possible while remaining non-destructive via the method herein.

For example, the determination of whether an endpoint has been reached in block 440, or whether it is final at block 450, could be performed by computer arrangement 250, shown in FIG. 2, in connection with the substrate removal arrangement 270. Once the depth of substrate removal is determined the substrate removal process can be controlled.

While the present invention has been described with reference to several particular example embodiments, those skilled in the art will recognize that many changes may be made thereto without departing from the spirit and scope of the present invention, which is set forth in the following claims.

What is claimed is:

1. A method for removing substrate from a semiconductor chip for post-manufacturing analysis, wherein the chip has a back side opposite circuitry near a circuit side, the method comprising selectively removing a portion of substrate in the back side of the semiconductor chip the thickness of the portion being determined as a function of detected sonic energy reflecting off of a region of the semiconductor chip.

2. A method for removing substrate from a semiconductor chip, according to claim 1, wherein removing a portion of substrate in the back side of the semiconductor chip as a function of sonic energy reflecting off of a region of the semiconductor chip comprises:

removing a portion of substrate in the back side of the semiconductor chip and forming an exposed region;
immersing the chip in liquid;
directing a sonic source at the back side;
detecting sonic energy reflecting off of the semiconductor chip via a detector; and
controlling the substrate removal responsive to the detected sonic energy.

3. The method of claim 2, wherein detecting sonic energy via a detector includes detecting sonic energy reflecting off of the back side of the chip.

4. The method of claim 2, wherein detecting sonic energy via a detector includes detecting sonic energy reflecting off of the exposed region.

5. The method of claim 2, wherein detecting sonic energy via a detector includes detecting sonic energy reflecting off of the circuitry.

6. The method of claim 2, wherein controlling the substrate removal responsive to the detected sonic energy comprises:

detecting the difference in time between sonic waves reflected off of the back side and off of the exposed region; and multiplying the difference in time by the speed of the wave and determining the amount of substrate that has been removed.

7. The method of claim 2, wherein controlling the substrate removal responsive to the detected sonic energy comprises:

detecting the difference in time between sonic waves reflected off of the exposed region and the circuitry; and multiplying the difference in time by the speed of the wave and determining the amount of substrate remaining between the exposed region and the circuitry.

8. The method of claim 2, wherein controlling the substrate removal includes programming a computer arrangement to use the detected sonic energy and to provide a control for the substrate removal.

9. A method for removing substrate from a semiconductor chip having a back side opposite circuitry near a circuit side, the method comprising the steps of:

(A) selectively removing substrate from the back side of the semiconductor chip;

(B) placing the semiconductor chip in a liquid;

(C) directing sonic energy at the chip and detecting substrate thickness therefrom;

(D) removing the chip from the liquid;

(E) repeating steps A through D until a the detected substrate thickness reaches an endpoint; and (F) responsive to reaching the endpoint, adjusting the substrate removal rate;

(G) repeating steps A through F until a final endpoint is detected; and (H) responsive to detecting the final endpoint, terminating the removal process.

* * * * *

UNITED STATES PATENT AND TRADEMARK OFFICE
CERTIFICATE OF CORRECTION

PATENT NO. : 6,350,624 B1
DATED : February 26, 2002
INVENTOR(S) : Goruganthu et al.

It is certified that error appears in the above-identified patent and that said Letters Patent is hereby corrected as shown below:

Title page,
Item [54], title should read "SUBSTRATE REMOVAL AS A FUNCTION OF SONIC ANALYSIS".

Drawings,
In Figure 3, "STENGTH" should read -- STRENGTH --.

Column 1,
Line 1, "FUNCTIONAL" should read -- FUNCTION --.
Line 22, "highdensity" should read -- high density --.

Column 8,
Line 16, after "until", please delete "a".

Signed and Sealed this

Twentieth Day of August, 2002

*Attest:*

JAMES E. ROGAN
*Director of the United States Patent and Trademark Office*

*Attesting Officer*